United States Patent
Li et al.

(10) Patent No.: US 9,040,727 B2
(45) Date of Patent: May 26, 2015

(54) HISTONE DEACETYLASE INHIBITOR OF BENZAMIDES AND USE THEREOF

(75) Inventors: Jianqi Li, Shanghai (CN); Qingwei Zhang, Shanghai (CN); Zhidan Jia, Jilin (CN); Jiajing Wang, Shanghai (CN)

(73) Assignees: Shanghai Institute of Pharmaceutical Industry (CN); Sinopharm A-Think Pharmaceutical Co., Ltd. (CN); Sinopharm A-Think Medical and Pharmaceutical Research & Development (Beijing) Co., Ltd. (CN)

( * ) Notice: Subject to any disclaimer, the term of this patent is extended or adjusted under 35 U.S.C. 154(b) by 0 days.

(21) Appl. No.: 14/129,407

(22) PCT Filed: Jun. 26, 2012

(86) PCT No.: PCT/CN2012/077521
§ 371 (c)(1),
(2), (4) Date: Apr. 9, 2014

(87) PCT Pub. No.: WO2013/000395
PCT Pub. Date: Jan. 3, 2013

(65) Prior Publication Data
US 2014/0221431 A1    Aug. 7, 2014

(30) Foreign Application Priority Data

Jun. 27, 2011 (CN) .......................... 2011 1 0175233

(51) Int. Cl.
| | | |
|---|---|---|
| A61K 31/4425 | (2006.01) | |
| C07C 237/48 | (2006.01) | |
| C07D 333/70 | (2006.01) | |
| C07D 235/24 | (2006.01) | |
| C07D 209/42 | (2006.01) | |
| C07D 307/85 | (2006.01) | |
| C07D 401/12 | (2006.01) | |
| C07D 405/12 | (2006.01) | |
| C07D 409/12 | (2006.01) | |
| C07C 237/42 | (2006.01) | |
| C07D 213/75 | (2006.01) | |
| C07D 307/87 | (2006.01) | |
| C07D 307/88 | (2006.01) | |

(52) U.S. Cl.
CPC ............ *C07C 237/48* (2013.01); *C07D 333/70* (2013.01); *C07D 235/24* (2013.01); *C07D 209/42* (2013.01); *C07D 307/85* (2013.01); *C07D 401/12* (2013.01); *C07D 405/12* (2013.01); *C07D 409/12* (2013.01); *C07C 237/42* (2013.01); *C07D 213/75* (2013.01); *C07D 307/87* (2013.01); *C07D 307/88* (2013.01)

(58) Field of Classification Search
CPC ............................ C07D 401/14; C07C 237/48
USPC ........................................ 514/339; 546/278.1
See application file for complete search history.

(56) References Cited

FOREIGN PATENT DOCUMENTS

| CN | 101899001 | | 12/2010 |
|---|---|---|---|
| JP | 10152462 | A * | 6/1998 |
| JP | 11302173 | A * | 11/1999 |
| WO | WO/2010/131922 | A2 * | 11/2010 |

OTHER PUBLICATIONS

King, Med. Chem. Principle and Practice (1994), pp. 206-208.*

* cited by examiner

*Primary Examiner* — Taofiq A Solola
(74) *Attorney, Agent, or Firm* — Stoel Rives LLP

(57) ABSTRACT

Disclosed in the present invention is a novel histone deacetylase inhibitor of benzamides and use thereof. The inhibitor has good efficacy in treating diseases caused by abnormal gene expression, such as tumors, endocrine disorders, immune system diseases, genetic diseases and nerve system diseases. The histone deacetylase inhibitor of benzamides is a compound of the following general chemical structural formula (I) or a salt thereof.

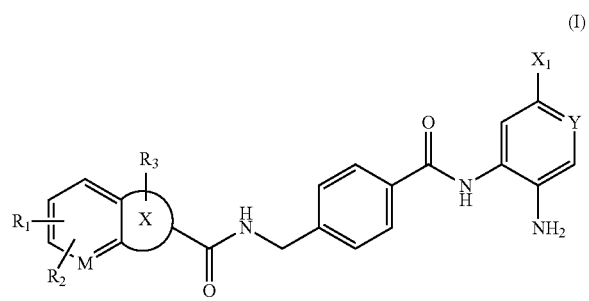

3 Claims, No Drawings

HISTONE DEACETYLASE INHIBITOR OF BENZAMIDES AND USE THEREOF

TECHNICAL FIELD

The present invention relates to a class of novel histone deacetylase inhibitors of benzamides and use of this class of small molecular compounds in the preparation of a medicament for treating malignant tumors and diseases related to cell differentiation and proliferation.

BACKGROUND

Acetylation and deacetylation of histones in the chromatin is a key step in regulating the gene expression, whereas abnormal gene expression constitutes the molecular biological basis for the occurrence of tumors and some hereditary and metabolic diseases. The acetylation degree of histones is co-regulated by histone acetylases (HATs) and histone deacetylases (HDACs). Overexpression of HDACs and the recruitment thereof by transcription factors would cause abnormal inhibition of specific genes, leading to tumors and other diseases (Grunstein, M., 1997, Nature, 389:349-352). The HDAC activity is reported to be related to the occurrence of cancers, immunological diseases, and some mental and cardiovascular diseases (Ruijter, A-J-M., 2003, Biochem. J., 370:737-749; Grignani, F., 1998, Nature, 391:815-818; Lin, R-J, 1998, 391:811-814; Marks, P-A., 2001, Nature Reviews Cancer, 1:194).

It is experimentally demonstrated that the inhibitor of HDACs can increase the level of acetylation of histones in the chromatin, accordingly causing the activation and expression of specific genes and in turn the terminal differentiation of cells or the apoptosis of cancer cells. Preliminary clinical research has shown that it is safe for a human to achieve a high acetylation level of histones by inhibiting the HDAC activity. Therefore, HDACs are of the newest and hottest targets in the current research and development area for chemotherapeutic drugs.

HDAC is an enzyme superfamily with its members known to occur in four classes comprising 18 different subtypes, wherein Class I comprises four subtypes, namely HDAC1, 2, 3, and 8; Class II comprises six subtypes, namely HDAC4, 5, 6, 7, 9, and 10 (wherein HDAC4, 5, 7, and 9 belong to Class IIa, and HDAC6 and 10 belong to Class IIb); Class IV only comprises one subtype, HDAC11 which shares certain homology with the previous two classes; Class III comprises seven subtypes in total including Sirt1-7 which do not share any structural homology with the previous three classes. At present, HDAC subtypes in Class I and Class II are relatively better studied, but not much is known about Class III and Class IV of HDACs. HDAC Class I proteins mainly localize in the nucleus and are expressed in cells of multiple tissues. HDAC Class II proteins mainly localize in the cytoplasm (or shuttle between the nucleus and the cytoplasm) and are only expressed in cells of some kinds of tissues. Results from research using small interfering RNA technique and animal gene knockout technique have shown comprehensively that some HDAC subtypes from Class I and Class IIa could be the target relevant to an antitumor effect, wherein inhibiting HDAC1, 2 and 3 can result in inhibition of cell proliferation; inhibiting HDAC4 can affect the repair processes of DNA damage; and inhibiting HDAC7 can induce apoptosis of thymocytes.

Research in recent years has fully demonstrated that the overexpression or abnormal activities of HDACs play an important role in the occurrence and development of leukemia and solid tumors. It is shown that significant in vivo and in vitro antitumor effects can be achieved by inhibiting the HDAC functional activity. HDAC inhibitors currently under investigation in clinical trials can be categorized into four groups based on their chemical structures, namely:

(1) hydroxamic acids, e.g. trichostatin (TSA), and suberolanilide hydroxamic acid (SAHA);
(2) cyclic tetrapeptides, e.g. Apicidin;
(3) short-chain or aromatic fatty acids, e.g. sodium butyrate; and
(4) benzamides, e.g. MS-275.

The first two groups of compounds are non-selective HDAC inhibitors and inhibit all HDAC subtypes in Class I and Class II. Short-chain or aromatic fatty acids generally have weaker inhibition activities and need to be tested in combination with other medicaments to provide stronger effects. Benzamides, however, are selective with targeting effects and mainly inhibit Class I HDACs (including HDAC subtypes 1, 2 and 3 but not HDAC8) and part of Class IIa HDACs and have no inhibitory effect on Class IIb HDACs. At present, antitumor drugs targeting HDACs are being investigated worldwide. SAHA (Trade name Zolinza) developed by Merk Company has been approved by FDA for treating cutaneous T-cell lymphoma (CTCL) and launched at the end of 2006. This not only indicates the end of the confirmatory research phase for the concept of using HDAC as a novel drug target, but also implies a broad prospect of developing HDAC inhibitors as novel antitumor drugs. Meanwhile, studies on the mechanisms underlying the antitumor effect of HDAC inhibitors are gradually going deeper and encompass multiple aspects related to the tumor formation and development such as induction of tumor cell apoptosis, inhibition of tumor cell cycle, induction of tumor cell differentiation, inhibition of angiogenesis, inhibition of tumor metastasis, and regulation of the immune system function etc.

Due to the structure similarity of the HDAC subtypes, most of the present HDAC inhibitors are not selective towards these subtypes and typically inhibit multiple subtypes at the same time, causing certain side effects and thus affecting the druggability of the inhibitors. Consequently, research focus and technical difficulty in the prior art of this area is to obtain a novel and effective anti-malignant tumor agent with low adverse side effects and high safety by designing and synthesizing highly selective HDAC inhibitors, especially the HDAC inhibitors of benzamides.

It is shown by the study that the structures of most of the HDAC inhibitors comprise an enzyme surface recognition domain, a linker region and a zinc-chelating region. Studies on the zinc-chelating region of the N-benzanilides indicate that 2'-amino group is the key group for the inhibitory activity, because the compound would lose its inhibitory activity when the 2'-amino group is removed and the 3'- or 4'-position on the aryl is substituted with an amino or acetylated amino group, indicating that an amino group at the ortho position is necessary for the compounds' inhibitory activities. The length, hydrophobicity and steric hindrance of the groups in the linker region and the enzyme surface recognition domain can also affect the inhibitory activity of the compound toward the enzyme. Studies on the linker region and the enzyme surface recognition domain have revealed that: the planar or SP2 configuration of the linking unit is essential for effective HDAC inhibition, so the aromatic ring (benzene ring) of rigid planar structure in the linker region should be kept; and the binding between the enzyme surface recognition domain and the target enzyme is achieved mainly through hydrogen bonding between the substituents and the amino acid residues, so the inhibitory activity of the compound can be enhanced by increasing the hydrophobicity of this domain. A series of novel building blocks can be obtained through diverse modifications of the substituents on the aromatic ring or the aromatic heterocyclic ring.

SUMMARY OF THE INVENTION

One of the technical problems to be solved by the present invention is to disclose a class of novel histone deacetylase inhibitors of benzamides to meet the need in the clinical application.

The histone deacetylase inhibitor of benzamides as disclosed herein refers to a compound of the following general chemical structural formula or a salt thereof:

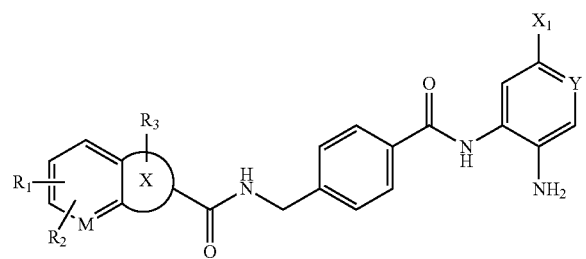

wherein:

X is a benzene ring, or a 5- or 6-membered heterocyclic ring with 1-2 heteroatoms;

$R_1$, $R_2$ or $R_3$ represents hydrogen, halogen, amino, hydroxy, nitro, cyano, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ amido, $C_1$-$C_4$ thioalkyl, trifluoromethyl, $C_1$-$C_4$ carboxyl, $C_1$-$C_4$ alkoxycarbonyl, phenyl, or heterocyclyl;

Y and M are each independently N or C;

$X_1$ is hydrogen, halogen, phenyl, or heterocyclyl;

when X is a 5-membered heterocyclic ring with one heteroatom selected from N, O or S, $R_1$, $R_2$ and $R_3$ are H, Y is C, and $X_1$ is H, then M is not N;

when X is a 5-membered heterocyclic ring with one heteroatom selected from N, O or S, Y is C, $X_1$ is H, and $R_3$ is H, then $R_1$ and $R_2$ are not —$NH_2$;

when X is a benzene ring, $R_1$, $R_2$ and $R_3$ are H, Y is C, and $X_1$ is H, then M is not N;

the heterocyclyl is a saturated or unsaturated heterocyclic ring containing one or more heteroatoms selected from the group consisting of N, O and S;

the halogen is preferably F, Cl, Br or I;

the $C_1$-$C_4$ alkyl is preferably methyl, ethyl, n-propyl, isopropyl, n-butyl, isobutyl, tert-butyl, or the like;

the $C_1$-$C_4$ alkoxy is preferably methoxy, ethoxy, n-propoxy, isopropoxy, n-butoxy, isobutoxy, or the like;

the $C_1$-$C_4$ aminoalkyl is preferably aminoethyl, 1-aminopropyl, 2-aminopropyl, or the like;

the $C_1$-$C_4$ alkylamino is preferably N-methylamino, N-ethylamino or N-isopropylamino;

the $C_2$-$C_4$ acyl is preferably acetyl, propionyl, isobutyryl, or the like;

the $C_2$-$C_4$ amido is preferably acetamido, propionamido, butanamido, isobutanamido, or the like;

the $C_1$-$C_4$ thioalkyl is preferably methylthio, ethylthio, propylthio, or the like;

said salt is a hydrochloride, hydrobromide, sulfate, acetate, lactate, tartrate, tannate, citrate, trifluoroacetate, malate, maleate, succinate, tosylate or mesylate;

said salt contains no crystal water, or one or more molecules of crystal water, preferably 0.5-3.0 molecules of crystal water.

Preferable compounds comprise:
V-1  N-(4-(2-aminophenylaminocarbonyl)phenyl)-2-naphthamide,
V-2  N-(4-(2-amino-5-fluorophenylaminocarbonyl)phenyl)-2-naphthamide,
V-2'  N-(4-(2-amino-5-fluorophenylaminocarbonyl)phenyl)-2-naphthamide hydrochloride,
V-3  N-(4-(2-aminophenylaminocarbonyl)phenyl)-6-methoxy-2-naphthamide,
V-4  N-(4-(2-amino-5-fluorophenylaminocarbonyl)phenyl)-6-methoxy-2-naphthamide,
V-5  N-(4-(2-aminophenylaminocarbonyl)phenyl)-1H-indole-2-carboxamide,
V-5'  N-(4-(2-aminophenylaminocarbonyl)phenyl)-1H-indole-2-carboxamide hydrobromide,
V-6  N-(4-(3-aminopyridine-4-carbamoyl)phenyl)-1H-indole-2-carboxamide,
V-6'  N-(4-(3-aminopyridine-4-carbamoyl)phenyl)-1H-indole-2-carboxamide sulfate,
V-7  N-(4-(2-amino-5-fluorophenylaminocarbonyl)phenyl)-1H-indole-2-carboxamide,
V-8  N-(4-(2-aminophenylaminocarbonyl)phenyl)benzofuran-2-carboxamide,
V-8'  N-(4-(2-aminophenylaminocarbonyl)phenyl)benzofuran-2-carboxamide mesylate,
V-9  N-(4-(2-amino-5-fluorophenylaminocarbonyl)phenyl)benzofuran-2-carboxamide,
V-10 N-(4-(2-amino-5-thienylphenylaminocarbonyl)phenyl)benzofuran-2-carboxamide,
V-11 N-(4-(2-amino-5-phenylphenylaminocarbonyl)phenyl)benzofuran-2-carboxamide,
V-12 N-(4-(2-aminophenylaminocarbonyl)phenyl)-1H-benzimidazol-2-carboxamide,
V-13 N-(4-(2-amino-5-fluorophenylaminocarbonyl)phenyl)-1H-benzimidazol-2-carboxamide,
V-13'  N-(4-(2-amino-5-fluorophenylaminocarbonyl)phenyl)-1H-benzimidazol-2-carboxamide trifluoroacetate,
V-14  N-(4-(2-amino-5-furylphenylaminocarbonyl)phenyl)-1H-benzimidazol-2-carboxamide,
V-15  N-(4-(2-aminophenylaminocarbonyl)phenyl)-1-naphthamide,
V-16  N-(4-(3-aminopyridine-4-carbamoyl)phenyl)-1-naphthamide,
V-17 N-(4-(2-amino-5-fluorophenylaminocarbonyl)phenyl)-1-naphthamide,
V-18 N-(4-(2-aminophenylaminocarbonyl)phenyl)-5-fluoro-1H-indole-2-carboxamide,
V-18'  N-(4-(2-aminophenylaminocarbonyl)phenyl)-5-fluoro-1H-indole-2-carboxamide malate,
V-19  N-(4-(2-aminophenylaminocarbonyl)phenyl)-5-methyl-1H-indole-2-carboxamide,
V-20  N-(4-(2-aminophenylaminocarbonyl)phenyl)-5-trifluoromethyl-1H-indole-2-carboxamide,
V-20'  N-(4-(2-aminophenylaminocarbonyl)phenyl)-5-trifluoromethyl-1H-indole-2-carboxamide maleate,
V-21  N-(4-(2-aminophenylaminocarbonyl)phenyl)-3-methoxybenzofuran-2-carboxamide,
V-22  N-(4-(2-aminophenylaminocarbonyl)phenyl)-5-methylamino-1H-indole-2-carboxamide,
V-23  N-(4-(2-aminophenylaminocarbonyl)phenyl)-5-amino-1H-indole-2-carboxamide,
V-24  N-(4-(2-aminophenylaminocarbonyl)phenyl)benzothiophene-2-carboxamide,
V-25  5-acetamido-N-(4-(2-aminophenylaminocarbonyl)phenyl)-1H-indole-2-carboxamide, V-26 5-acetyl-N-(4-(2-aminophenylaminocarbonyl)phenyl)-1H-indole-2-carboxamide, V-27 N-(4-(2-amino-5-fluorophenylaminocarbonyl)phenyl)benzothiophene-2-carboxamide, and V-28 N-(4-(3-aminopyridine-4-carbamoyl)phenyl)benzothiophene-2-carboxamide.

The structures of the foresaid compounds V-1 to V-28 are as follows:

| Serial number | Structure |
|---|---|
| V-1 | 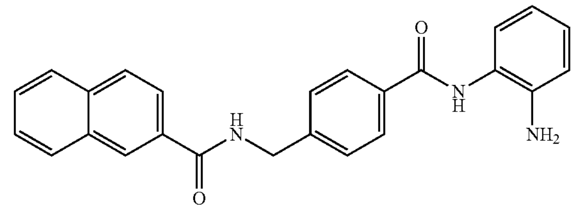 [SMILES: Nc1ccccc1NC(=O)c1ccc(CNC(=O)c2ccc3ccccc3c2)cc1] |
| V-2 | 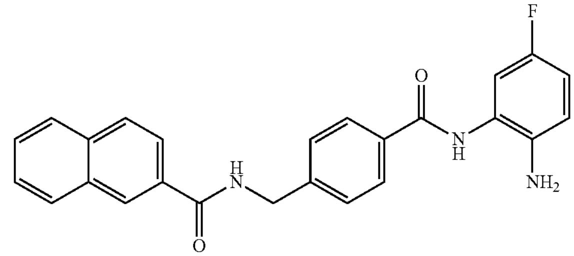 [SMILES: Nc1ccc(F)cc1NC(=O)c1ccc(CNC(=O)c2ccc3ccccc3c2)cc1] |
| V-3 | 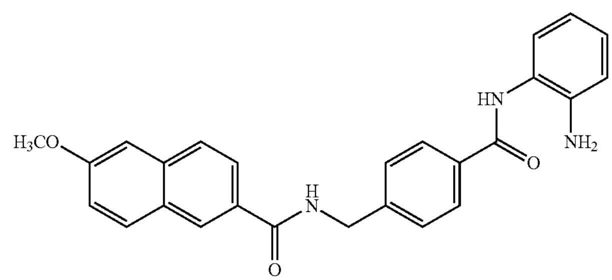 [SMILES: COc1ccc2cc(C(=O)NCc3ccc(C(=O)Nc4ccccc4N)cc3)ccc2c1] |
| V-4 | 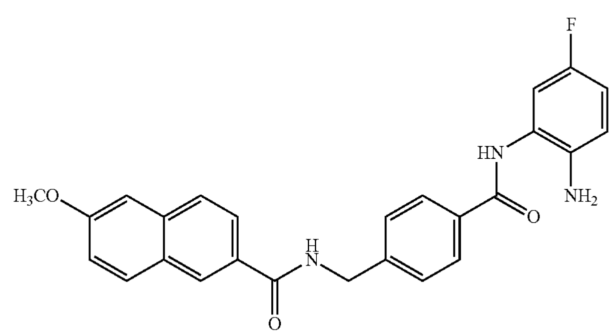 [SMILES: COc1ccc2cc(C(=O)NCc3ccc(C(=O)Nc4cc(F)ccc4N)cc3)ccc2c1] |
| V-5 | 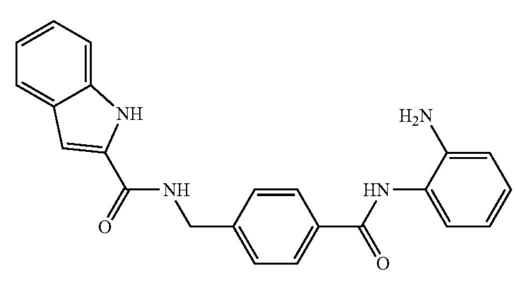 [SMILES: Nc1ccccc1NC(=O)c1ccc(CNC(=O)c2cc3ccccc3[nH]2)cc1] |

| Serial number | Structure |
|---|---|
| V-6 | 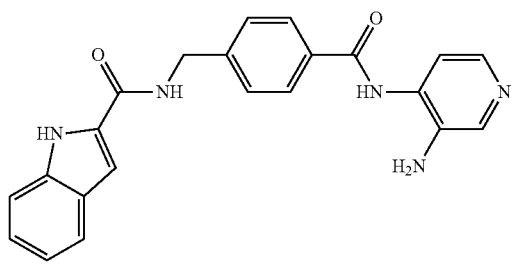 [SMILES: Nc1cnccc1NC(=O)c1ccc(CNC(=O)c2cc3ccccc3[nH]2)cc1] |
| V-7 | 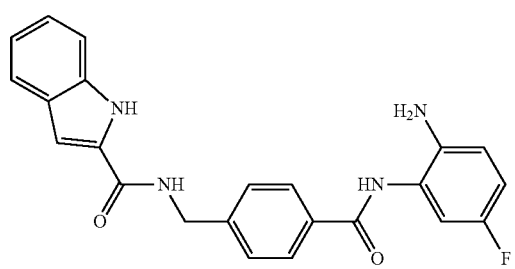 [SMILES: Nc1ccc(F)cc1NC(=O)c1ccc(CNC(=O)c2cc3ccccc3[nH]2)cc1] |
| V-8 | 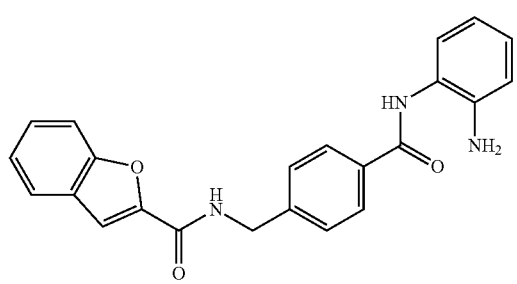 [SMILES: Nc1ccccc1NC(=O)c1ccc(CNC(=O)c2cc3ccccc3o2)cc1] |
| V-9 | 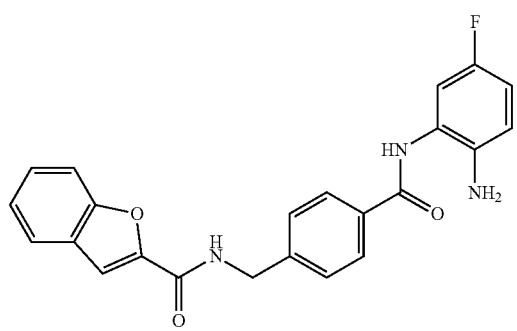 [SMILES: Nc1ccc(F)cc1NC(=O)c1ccc(CNC(=O)c2cc3ccccc3o2)cc1] |
| V-10 | 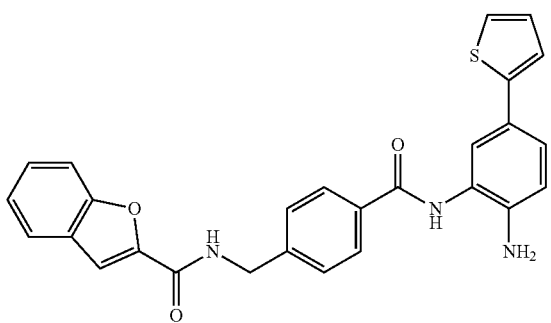 [SMILES: Nc1ccc(-c2cccs2)cc1NC(=O)c1ccc(CNC(=O)c2cc3ccccc3o2)cc1] |

-continued
| Serial number | Structure |
|---|---|
| V-11 | 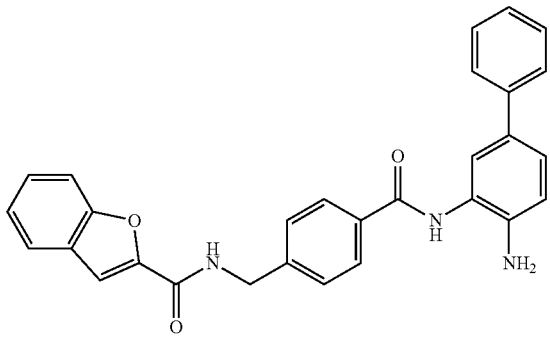 [SMILES: Nc1ccc(-c2ccccc2)cc1NC(=O)c1ccc(CNC(=O)c2cc3ccccc3o2)cc1] |
| V-12 | 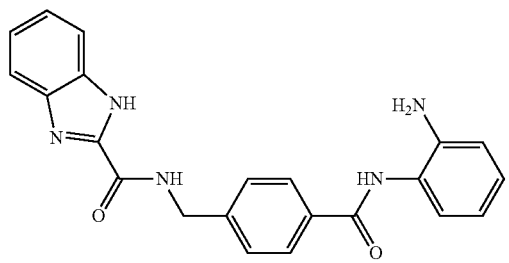 [SMILES: Nc1ccccc1NC(=O)c1ccc(CNC(=O)c2nc3ccccc3[nH]2)cc1] |
| V-13 | 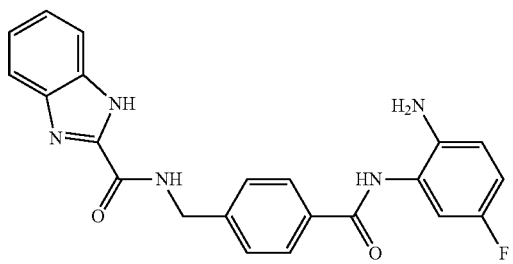 [SMILES: Nc1ccc(F)cc1NC(=O)c1ccc(CNC(=O)c2nc3ccccc3[nH]2)cc1] |
| V-14 | 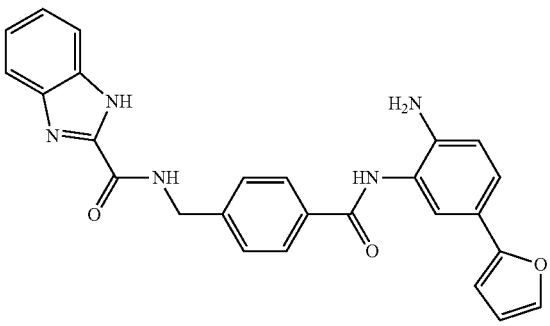 [SMILES: Nc1ccc(-c2ccco2)cc1NC(=O)c1ccc(CNC(=O)c2nc3ccccc3[nH]2)cc1] |
| V-15 | 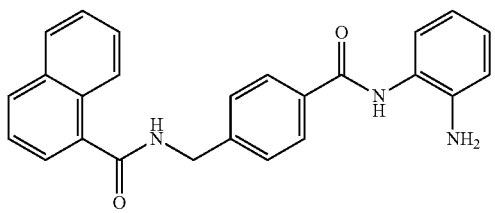 [SMILES: Nc1ccccc1NC(=O)c1ccc(CNC(=O)c2cccc3ccccc23)cc1] |

-continued
| Serial number | Structure |
|---|---|
| V-16 | 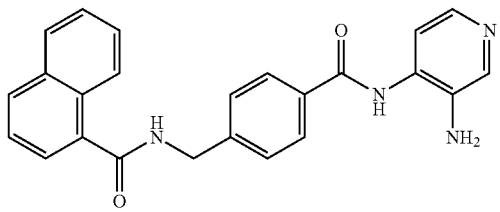 [SMILES: Nc1cnccc1NC(=O)c1ccc(CNC(=O)c2cccc3ccccc23)cc1] |
| V-17 | 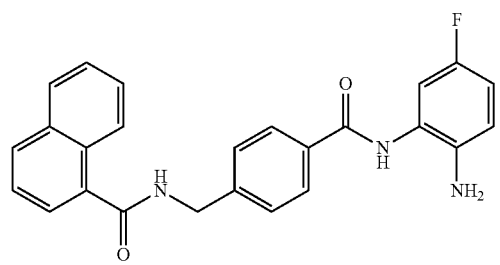 [SMILES: Nc1ccc(F)cc1NC(=O)c1ccc(CNC(=O)c2cccc3ccccc23)cc1] |
| V-18 | 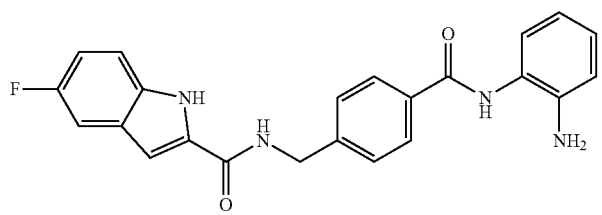 [SMILES: Nc1ccccc1NC(=O)c1ccc(CNC(=O)c2cc3cc(F)ccc3[nH]2)cc1] |
| V-19 | 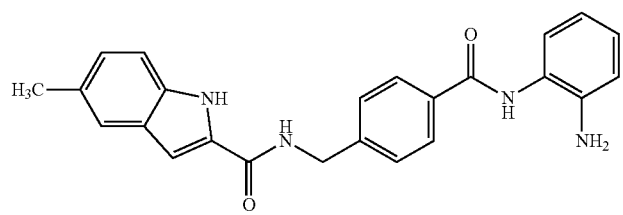 [SMILES: Nc1ccccc1NC(=O)c1ccc(CNC(=O)c2cc3cc(C(F)(F)F)ccc3[nH]2)cc1] |
| V-20 | 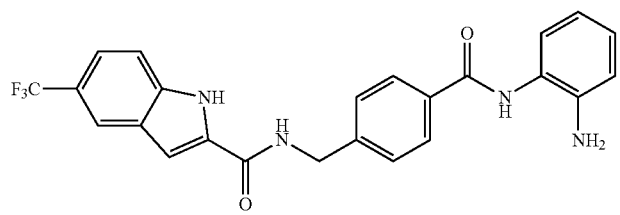 |
| V-21 | 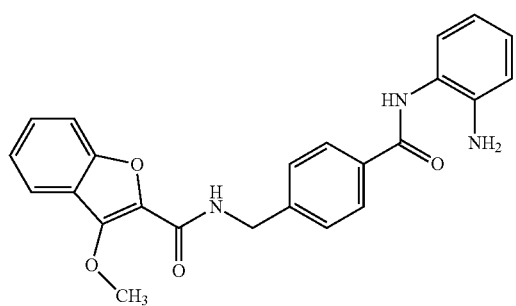 [SMILES: COc1c(C(=O)NCc2ccc(C(=O)Nc3ccccc3N)cc2)oc2ccccc12] |

-continued
| Serial number | Structure |
|---|---|
| V-22 | 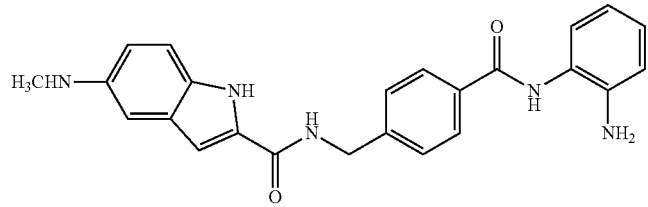 |
| V-23 | 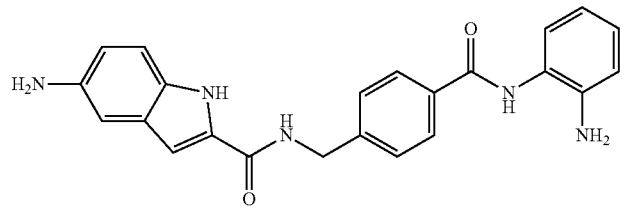 |
| V-24 | 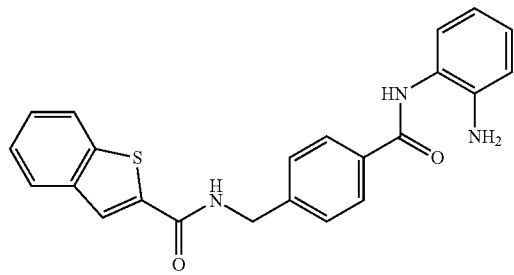 |
| V-25 | 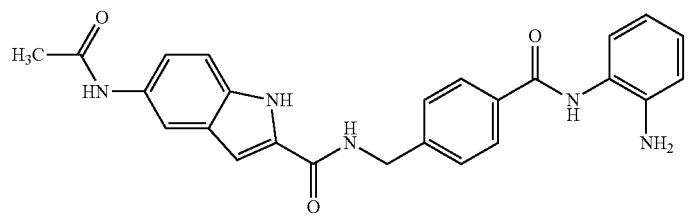 [SMILES: CC(=O)Nc1ccc2[nH]c(C(=O)NCc3ccc(C(=O)Nc4ccccc4N)cc3)cc2c1] |
| V-26 | 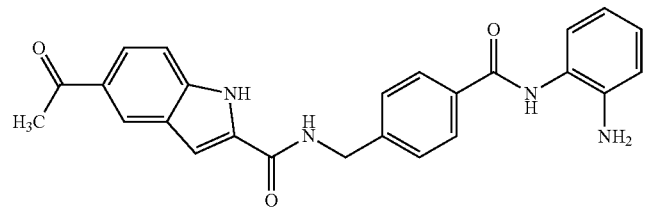 [SMILES: CC(=O)c1ccc2[nH]c(C(=O)NCc3ccc(C(=O)Nc4ccccc4N)cc3)cc2c1] |
| V-27 | 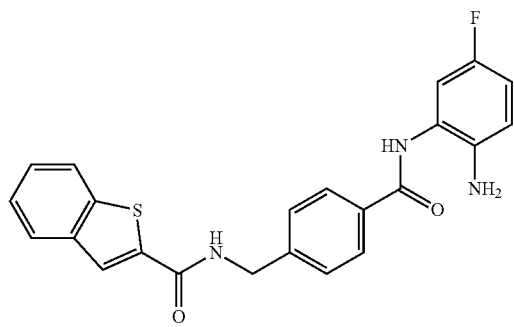 |

| Serial number | Structure |
|---|---|
| V-28 | 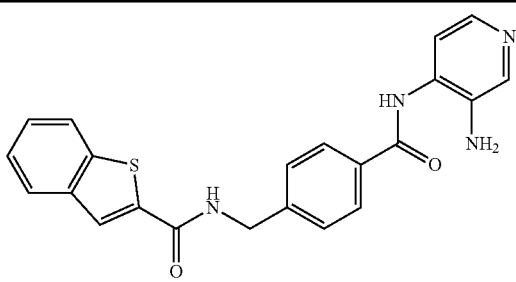 |
The structures of the foresaid compounds V-2', V-5', V-6', V-8', V-13', V-18' and V-20' are as follows:
V-2'
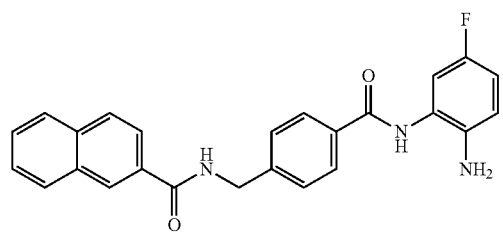
·HCl
V-5'
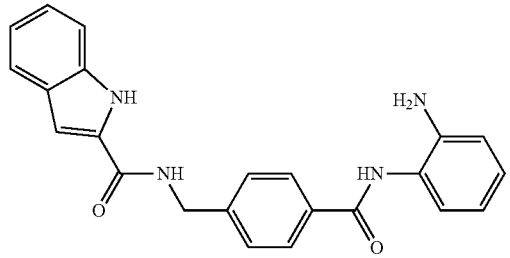
·HBr
V-6'
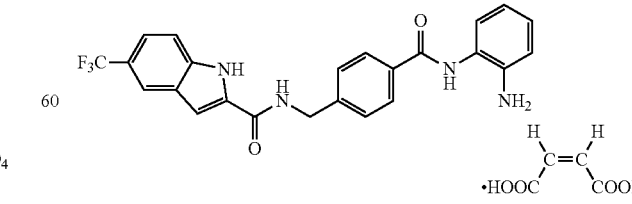
·H₂SO₄
V-8'
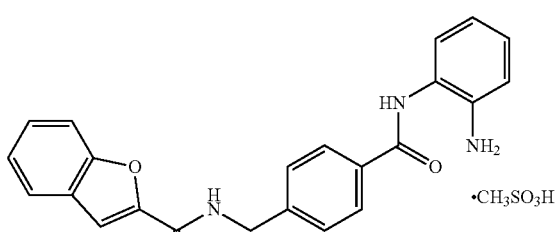
·CH₃SO₃H
V-13'
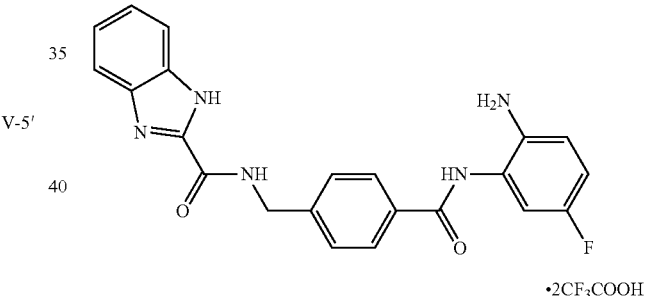
·2CF₃COOH
V-18'
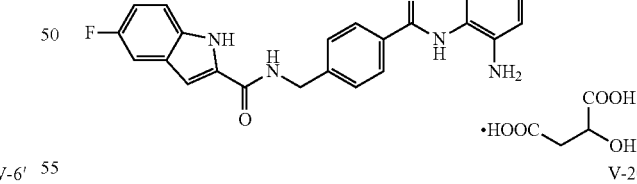
·HOOC—CH(OH)—COOH
V-20'
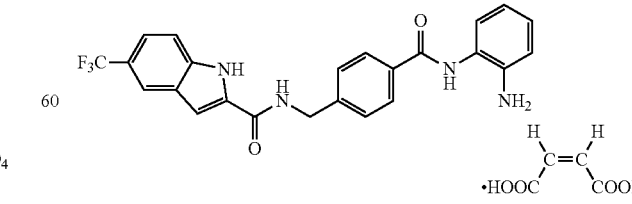
·HOOC—CH=CH—COOH
The compound of the present invention can be synthesized by the following methods:

General Method I:

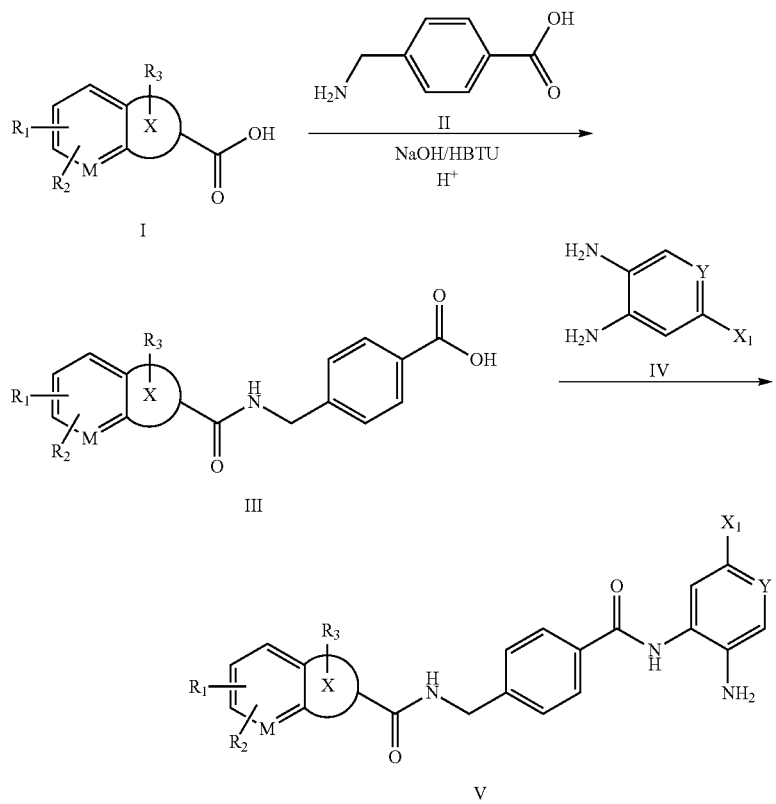

Substituted acid I (50 mmol) and O-(1H-benzotriazol-1-yl)-N,N,N',N'-tetramethylisouronium hexafluorophosphate (HBTU) (18.95 g, 50 mmol) are added into acetonitrile, and slowly added with triethylamine (10.1 g, 100 mmol) in a dropwise manner while being kept in an ice bath. Stir at ambient temperature for 1 h to provide a homogeneous reaction mixture, which is added dropwise at the reaction temperature into a solution of p-aminomethylbenzoic acid II (50 mmol) in 10 ml 1 mol/L sodium hydroxide aqueous solution. Upon the completion of addition, the reaction mixture is stirred at constant temperature for 6 h, and then added with concentrated HCl to adjust the pH so as to precipitate a great quantity of solid which is filtered and dried to give Intermediate III.

Intermediate III (1 mmol), Compound IV (1 mmol), and HBTU (0.379 g, 1 mmol) are added sequentially into 10 ml N,N-dimethyl formamide, and added with triethylamine (2 mmol) dropwise while being kept in an ice bath. The reaction mixture is then stirred at room temperature for 4 h. Subsequently, the reaction mixture is poured into ice water, adjusted with HCl to a pH of about 7-9, and extracted with dichloromethane. The organic phase is dried over anhydrous magnesium sulphate, filtered and concentrated. The residue is purified through column chromatography or recrystallization to provide the target compound V.

Corresponding salt of Compound V can be obtained by cooling and filtering the reaction mixture resulting from stirring Compound V with inorganic or organic acid in anhydrous ethanol or ethyl acetate.

$R_1$, $R_2$, $R_3$, X, Y, $X_1$ and M in the above General Method have the same meanings as described before;

Compounds I, II, IV and HBTU etc. are commercially available.

It is demonstrated by the pharmacological experiment that, the compound or a salt thereof according to the present invention has very strong inhibitory effect on the tumor-associated HDAC subtype, HDAC1 (Example 29), exhibiting inhibitory activities superior or comparable to a similar drug currently being investigated in an abroad clinical trial, MS-275, at concentrations of 10 μM and 1 μM.

The $IC_{50}$ values for the in vitro inhibitory effect on histone deacetylases (HDACs) indicate that, Compounds V-5, V-8, V-15, V-16, V-17, V-19, V-20 and V-24 etc. have better inhibitory activities than MS-275. For example, the $IC_{50}$ value of V-8 against HDACs is 1.83 μM and the $IC_{50}$ value of MS-275 against HDACs is 3.52 μM. The $IC_{50}$ values for the inhibitory effect on the tumor-associated HDAC subtype, HDAC1 indicate that, Compounds V-5, V-6, V-9, V-14, V-15, V-16, V-19, V-25, V-26 and V-27 have better inhibitory activities against HDAC1 as compared with MS-275. For example, the $IC_{50}$ value of V-5 against HDAC1 is 210 nM, significantly superior to that of MS-275 ($IC_{50}$=668 nM), indicating a stronger targeting capacity towards HDAC subtypes.

It is demonstrated by the pharmacological experiment that, the compound or a salt thereof according to the present invention shows stronger differentiation induction and anti-proliferative effects on multiple strains of tumor cells. Especially, for Hut78 T lymphocytic leukemia cells, Jurkat E6-1 human T-cell lymphoma, A549 human lung cancer cells, K562 human chronic myelogenous leukemia cells, Hep3B2.1-7 human liver cancer cells, MDA-MB-435s human breast cancer cells, Colo320 human rectal cancer cell line, and PC-3 human prostate cancer, the anti-proliferative effects are significant (Example 30). The $IC_{50}$ values for the in vitro inhibitory effect on the proliferation of tumor cell strains indicate that, all the tested compounds have better anti-proliferation effects. Compounds V-5, V-6, V-14, V-19, V-25, V-27 and the like show higher inhibition rate for multiple strains of tumor cells as compared with MS-275. For example, as compared with MS-275, Compound V-5 shows significantly stronger inhibitory effect against tumor cells such as Hut78, K562, and Jurkat E6-1, especially for Hut78, in which case $IC_{50}$ is 0.0194 μM, significantly better than MS-275 ($IC_{50}$=0.5281 μM).

It is demonstrated by the pharmacological experiment that, the compound or a salt thereof according to the present invention is less toxic. The maximum tolerance doses of Compounds V-5, V-6, V-9, V-14, V-16, V-19, V-25, V-26, V-27 when administered intragastrically are over 2000 mg/kg in mice (Example 31).

It is demonstrated by the pharmacological experiment that, the compound or a salt thereof according to the present invention has smaller cardiotoxicity than another HDAC inhibitor SAHA. For example, the $IC_{50}$ values of Compounds V-5 and V-9 for their effects on hERG potassium current are both above 10 μM, indicating a better cardiac safety (Example 32).

It is demonstrated by the pharmacological experiment that, the compound or a salt thereof according to the present invention provides promising preliminary pharmacokinetic data, showing longer intravenous half-life (1-2 h), higher oral bioavailability, and better druggability (Example 33).

In conclusion, the compound or a salt thereof according to the present invention not only has distinct inhibitory effect on HDACs and the tumor-associated subtype thereof, HDAC1, but also has stronger differentiation induction and anti-proliferative activities for multiple strains of tumor cells. When compared to a similar drug currently being investigated in an abroad clinical trial, MS-275, the compound of the present invention has apparent advantages in its inhibitory activity or antitumor activity, and more than that, it has the following advantages: smaller toxicity, higher cardiac safety, better preliminary pharmacokinetic data, and better druggability. The development of the compound or a salt thereof according to the present invention to a medicament for treating cancers and diseases related to cell differentiation and proliferation is novel, inventive and practical, and worth further investigation.

The present invention further relates to a composition comprising a therapeutically effective amount of the compound or a salt thereof according to the present invention and a pharmaceutically acceptable carrier, wherein the carrier can be any substances commonly used as a carrier such as flavors, sweeteners, liquid or solid fillers, diluents or the like, and the composition of the invention can be formulated with a method well-known in this field into a common pharmaceutical formulation such as in the form of tablet, capsule, powder, syrup, liquid, suspension or injection, typically comprising 1-70% by weight and preferably 5-50% by weight of the active ingredient.

Clinically, the compound according to the present invention can be administrated orally or by injection to a mammal (including human), wherein oral administration is mostly preferred. The administration dose can be 0.0001-200 mg/kg body weight per day. The optimal dose varies depending on the individuals, usually starting with a smaller dose and gradually increasing the amount.

The feature of the present invention is that the enzyme surface recognition domain of the HDAC inhibitor of benzamides is substituted with a series of fused-heterocycles for the purpose of increasing the spatial matching between the compound and the recognition domain on the surface of the enzyme, especially for increasing the binding affinity of the compound to an enzyme subtype. After screening for inhibition of the enzyme subtype HDAC1, it is found that the inhibitory activity of this kind of compound towards HDAC1 is significantly improved, indicating that the recognition domain on the surface of HDAC1 has relatively larger spatial tolerance, and has key amino acid residues useful for specific recognition and binding with substituents on the fused-heterocycle, such as —NH—, —O— or the like. It is thus predicted that an HDAC inhibitor of benzamides with much stronger inhibitory activities towards an enzyme subtype can be obtained by modifying its enzyme surface recognition domain with different heterocycles or structures carrying different substituents on a heterocycle. The study thus provides theoretical guidance for the development of a novel and effective anti-tumor medicament with low adverse side effects and high safety and possessing the druggability. The present invention is novel, inventive and scientifically advanced over the prior art.

The advantage of the present invention is that said compound and the pharmaceutical formulation thereof have a very good efficacy in treating diseases caused by abnormal gene expression such as tumors, endocrine disorders, immune system diseases, genetic diseases and nervous system diseases.

EMBODIMENTS OF THE INVENTION

The present invention will be further illustrated below by reference to the following Examples. It is to be understood that this invention is not limited to the Examples. All percentages present in the present invention are weight percentages, unless otherwise specified.

EXAMPLE 1

V-1 N-(4-(2-aminophenylaminocarbonyl)phenyl)-2-naphthamide

Following the General Method for the preparation of the intermediate III, a white solid (Intermediate M-1) of the weight 2.47 g was obtained with 2-naphthoic acid (1.72 g, 10 mmol) and p-aminomethylbenzoic acid (1.51 g, 10 mmol)

Following the General Method for the preparation of the final product V, a white solid of the weight 0.231 g was obtained with M-1 (0.305 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=396

1H-NMR (400 MHz, DMSO-d6) δ ppm: 4.61 (d, 2H, J=6.0 Hz), 4.84 (s, 2H), 6.60 (t, 1H, J=7.2 Hz), 6.78 (d, 1H, J=8.0 Hz), 6.97 (t, 1H, J=7.2 Hz), 7.18 (d, 1H, J=7.6 Hz), 7.49 (d, 2H, J=8.0 Hz), 7.62 (m, 2H), 8.02 (m, 6H), 8.52 (s, 1H), 9.22 (t, 1H, J=6.0 Hz), 9.56 (s, 1H)

EXAMPLE 2

V-2 N-(4-(2-amino-5-fluorophenylaminocarbonyl)phenyl)-2-naphthamide

Following the General Method for the preparation of the final product V, a white solid V-2 of the weight 0.19 g was obtained with M-1 (0.305 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

The above white solid V-2 is heated to dissolve in 3 mol/L hydrochloric acid/ethanol solution (10 ml) and cooled to precipitate the hydrochloride of V-2, compound V-2' having a total weight of 0.11 g.

MS (ESI): [M+H]+=414

1H-NMR (400 MHz, DMSO-d6) δ ppm: 4.56 (d, 2H, J=6.0 Hz), 5.10 (s, 2H), 6.31 (dt, 1H, J=2.8 Hz, 8.4 Hz), 6.49 (dd, 1H, J=2.8 Hz, 10.8 Hz), 7.08 (t, 1H, J=7.2 Hz), 7.43 (d, 1H, J=8.4 Hz), 7.56 (m, 2H), 7.96 (m, 6H), 8.46 (s, 1H), 9.17 (t, 1H, J=8.0 Hz), 9.45 (s, 1H)

EXAMPLE 3

V-3 N-(4-(2-aminophenylaminocarbonyl)phenyl)-6-methoxy-2-naphthamide

Following the General Method for the preparation of the intermediate III, a white solid (Intermediate M-2) of the weight 2.51 g was obtained with 6-methoxy-2-naphthoic acid (2.02 g, 10 mmol) and p-aminomethylbenzoic acid (1.51 g, 10 mmol).

Following the General Method for the preparation of the final product V, a white solid of the weight 0.31 g was obtained with M-2 (0.335 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=425

1H-NMR (400 MHz, DMSO-d6) δ ppm: 3.85 (s, 3H), 4.54 (d, 2H, J=6.0 Hz), 4.77 (s, 2H), 6.55 (dt, 1H, J=1.2 Hz, 7.6 Hz), 6.73 (dd, 1H, J=1.2 Hz, 7.6 Hz), 6.90 (dt, 1H, J=1.2 Hz, 7.6 Hz), 7.18 (m, 2H), 7.33 (d, 1H, J=2.4 Hz), 7.42 (d, 2H, J=8.0 Hz), 7.88 (m, 5H), 8.38 (s, 1H), 9.08 (t, 1H, J=6.0 Hz), 9.51 (s, 1H)

EXAMPLE 4

V-4 N-(4-(2-amino-5-fluorophenylaminocarbonyl)phenyl)-6-methoxy-2-naphthamide

Following the General Method for the preparation of the final product V, a white solid of the weight 0.37 g was obtained with M-2 (0.335 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=444

1H-NMR (400 MHz, DMSO-d6) δ ppm: 3.85 (s, 3H), 4.54 (d, 2H, J=6.0 Hz), 5.10 (s, 2H), 6.30 (dt, 1H, J=2.8 Hz, 8.4 Hz), 6.49 (dd, 1H, J=2.8 Hz, 11.2 Hz), 7.06 (dt, 1H, J=2.0 Hz, 7.6 Hz), 7.18 (dd, 1H, J=2.4 Hz, 8.8 Hz), 7.33 (d, 1H, J=2.4 Hz), 7.42 (d, 2H, J=8.4 Hz), 7.88 (m, 5H), 8.38 (s, 1H), 9.07 (t, 1H, J=6.0 Hz), 9.45 (s, 1H)

EXAMPLE 5

V-5 N-(4-(2-aminophenylaminocarbonyl)phenyl)-1H-indole-2-carboxamide

Following the General Method for the preparation of the intermediate III, a white solid (Intermediate M-3) of the weight 2.11 g was obtained with indole-2-carboxylic acid (1.61 g, 10 mmol) and p-aminomethylbenzoic acid (1.51 g, 10 mmol).

Following the General Method for the preparation of the final product V, a white solid V-5 of the weight 0.29 g was obtained with M-3 (0.294 g, 1 mmol), o-phenylenediamine (0.108 g, 1 mmol), HBTU (0.379 g, 1 mmol), N,N-dimethylformamide (10 ml), and triethylamine (0.202 g, 2 mmol).

The above white solid V-5 of 0.21 g is dissolved in hot ethanol, followed by adding 4 mol/L hydrobromic acid/ethyl acetate solution (2 ml) dropwise and cooling to precipitate 0.11 g of the hydrobromide of V-5, compound V-5' as a white solid.

MS (ESI): [M+H]+=385

1H-NMR (400 MHz, DMSO-d6) δ ppm: 4.53 (d, 2H, J=6.4 Hz), 4.77 (s, 2H), 6.55 (dt, 1H, J=1.2 Hz, 7.6 Hz), 6.73 (dd, 1H, J=1.2 Hz, 7.6 Hz), 6.99 (dt, 1H, J=0.8 Hz, 8.0 Hz), 7.13 (m, 3H), 7.41 (m, 3H), 7.46 (d, 1H, J=8.0 Hz), 7.89 (d, 2H, J=8.0 Hz), 8.98 (t, 1H, J=6.0 Hz), 9.51 (s, 1H), 11.47 (s, 1H)

EXAMPLE 6

V-6 N-(4-(3-aminopyridine-4-carbamoyl)phenyl)-1H-indole-2-carboxamide

Following the General Method for the preparation of the final product V, a white solid of the weight 0.27 g was obtained with M-3 (0.294 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol)

The above white solid V-6 of 0.20 g is dissolved in hot ethanol, followed by slowly adding 98% sulfuric acid (1 ml) dropwise and cooling to precipitate 0.11 g of the sulfate of V-6, compound V-6' as a white solid.

MS (ESI): [M+H]+=386

1H-NMR (400 MHz, DMSO-d6) δ ppm: 4.53 (d, 2H, J=6.4 Hz), 5.05 (s, 2H), 6.98 (t, 1H, J=7.2 Hz), 7.13 (t, 2H, J=8.0 Hz), 7.40 (m, 4H), 7.56 (d, 1H, J=8.0 Hz), 7.74 (d, 1H, J=5.2 Hz), 7.88 (d, 1H, J=8.0 Hz), 8.04 (s, 1H), 8.99 (t, 1H, J=6.0 Hz), 9.60 (s, 1H), 11.47 (s, 1H)

EXAMPLE 7

V-7 N-(4-(2-amino-5-fluorophenylaminocarbonyl)phenyl)-1H-indole-2-carboxamide

Following the General Method for the preparation of the final product V, a white solid of the weight 0.22 g was obtained with M-3 (0.294 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=403

1H-NMR (400 MHz, DMSO-d6) δ ppm: 4.53 (d, 2H, J=6.0 Hz), 5.09 (s, 2H), 6.30 (dt, 1H, J=2.8 Hz, 8.8 Hz), 6.49 (dd, 1H, J=2.8 Hz, 11.2 Hz), 6.98 (dt, 1H, J=0.8 Hz, 8.0 Hz), 7.06 (dt, 1H, J=2.4 Hz, 8.8 Hz), 7.13 (m, 2H), 7.40 (m, 3H), 7.57 (d, 1H, J=8.0 Hz), 7.89 (d, 2H, J=8.0 Hz), 8.98 (t, 1H, J=6.0 Hz), 9.45 (s, 1H), 11.47 (s, 1H)

EXAMPLE 8

V-8 N-(4-(2-aminophenylaminocarbonyl)phenyl)benzofuran-2-carboxamide

Following the General Method for the preparation of the intermediate III, a white solid (intermediate M-4) of the weight 2.07 g was obtained with benzofuran-2-carboxylic acid (1.62 g, 10 mmol) and p-aminomethylbenzoic acid (1.51 g, 10 mmol).

Following the General Method for the preparation of the final product V, a white solid of the weight 0.27 g was obtained with M-4 (0.295 g, 1 mmol), o-phenylenediamine (0.108 g, 1 mmol), HBTU (0.379 g, 1 mmol), N,N-dimethylformamide (10 ml), and triethylamine (0.202 g, 2 mmol).

The above white solid V-8 of 0.24 g is dissolved in hot ethanol, followed by adding methylsulfonic acid/ethanol solution dropwise, refluxing for 30 min and cooling to precipitate 0.17 g of the mesylate of V-8, compound V-8' as a yellow solid.

MS (ESI): [M+H]+=386
1H-NMR (400 MHz, DMSO-d6) δ ppm: 4.53 (d, 2H, J=6.4 Hz), 4.77 (s, 2H), 6.55 (dt, 1H, J=1.2 Hz, 7.6 Hz), 6.70 (dd, 1H, J=1.2 Hz, 7.6 Hz), 6.99 (dt, 1H, J=1.2 Hz, 8.0 Hz), 7.13 (m, 3H), 7.41 (m, 3H), 7.46 (d, 1H, J=8.0 Hz), 7.89 (d, 2H, J=8.0 Hz), 8.98 (t, 1H, J=6.0 Hz), 9.51 (s, 1H)

EXAMPLE 9

V-9 N-(4-(2-amino-5-fluorophenylaminocarbonyl)phenyl)benzofuran-2-carboxamide

Following the General Method for the preparation of the final product V, a white solid of the weight 0.25 g was obtained with M-4 (0.295 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=386
1H-NMR (400 MHz, DMSO-d6) δ ppm: 4.50 (d, 2H, J=6.0 Hz), 4.77 (s, 2H), 6.55 (dt, 1H, J=1.6 Hz, 7.2 Hz), 6.99 (dt, 1H, J=1.2 Hz, 8.0 Hz), 7.13 (m, 3H), 7.41 (m, 3H), 7.46 (d, 1H, J=8.0 Hz), 7.79 (d, 2H, J=8.0 Hz), 8.92 (t, 1H, J=6.0 Hz), 9.61 (s, 1H).

EXAMPLE 10

V-10 N-(4-(2-amino-5-thienylphenylaminocarbonyl)phenyl)benzofuran-2-carboxamide

Following the General Method for the preparation of the final product V, a white solid of the weight 0.33 g was obtained with M-4 (0.295 g, 1 mmol), 4-(2-thienyl)-1,2-phenylenediamine (0.190 g, 1 mmol), HBTU (0.379 g, 1 mmol), N,N-dimethylformamide (10 ml), and triethylamine (0.202 g, 2 mmol).

MS (ESI): [M+H]+=467
1H-NMR (400 MHz, DMSO-d6) δ ppm: 4.49 (d, 2H, J=6.0 Hz), 4.87 (s, 2H), 6.51 (dt, 1H, J=1.2 Hz, 7.6 Hz), 6.99 (dt, 1H, J=1.2 Hz, 8.0 Hz), 7.13 (m, 3H), 7.41 (m, 3H), 7.46 (m, 3H), 7.81 (d, 2H, J=8.0 Hz), 8.98 (t, 1H, J=6.0 Hz), 10.11 (s, 1H)

EXAMPLE 11

V-11 N-(4-(2-amino-5-phenylphenylaminocarbonyl)phenyl)benzofuran-2-carboxamide

Following the General Method for the preparation of the final product V, a white solid of the weight 0.37 g was obtained with M-4 (0.295 g, 1 mmol), 4-phenyl-1,2-phenylenediamine (0.184 g, 1 mmol), HBTU (0.379 g, 1 mmol), N,N-dimethylformamide (10 ml), and triethylamine (0.202 g, 2 mmol).

MS (ESI): [M+H]+=462
1H-NMR (400 MHz, DMSO-d6) δ ppm: 4.53 (d, 2H, J=6.4 Hz), 4.77 (s, 2H), 6.55 (dt, 1H, J=1.2 Hz, 7.6 Hz), 6.99 (dt, 1H, J=1.2 Hz, 8.0 Hz), 7.13 (m, 3H), 7.41 (m, 3H), 7.54 (m, 4H), 7.41 (d, 1H, J=8.0 Hz), 7.79 (d, 2H, J=8.0 Hz), 8.98 (t, 1H, J=6.0 Hz), 9.71 (s, 1H)

EXAMPLE 12

V-12 N-(4-(2-aminophenylaminocarbonyl)phenyl)-1H-benzimidazol-2-carboxamide

Following the General Method for the preparation of the intermediate III, a white solid (Intermediate M-5) of the weight 2.17 g was obtained with benzimidazol-2-carboxylic acid (1.62 g, 10 mmol) and p-aminomethylbenzoic acid (1.51 g, 10 mmol).

Following the General Method for the preparation of the final product V, a white solid of the weight 0.30 g was obtained with M-5 (0.295 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=386
1H-NMR (400 MHz, DMSO-d6) δ ppm: 4.63 (d, 2H, J=6.0 Hz), 4.79 (s, 2H), 6.45 (dt, 1H, J=1.2 Hz, 7.6 Hz), 6.70 (dd, 1H, J=1.2 Hz, 7.6 Hz), 6.89 (dt, 1H, J=1.2 Hz, 8.0 Hz), 7.10 (m, 3H), 7.37 (m, 3H), 7.46 (d, 1H, J=8.0 Hz), 7.89 (d, 2H, J=8.0 Hz), 8.98 (t, 1H, J=6.0 Hz), 9.47 (s, 1H), 11.55 (s, 1H)

EXAMPLE 13

V-13 N-(4-(2-amino-5-fluorophenylaminocarbonyl)phenyl)-1H-benzimidazol-2-carboxamide Following the General Method for the preparation of the final product V, a white solid of the weight 0.35 g was obtained with M-5 (0.295 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

The above white solid V-13 of 0.20 g is dissolved in hot ethanol, followed by adding trifluoroacetic acid/ethyl acetate solution dropwise and cooling to precipitate 0.14 g of the trifluoroacetate of V-13, compound V-13' as a white solid.

MS (ESI): [M+H]+=404
1H-NMR (400 MHz, DMSO-d6) δ ppm: 4.50 (d, 2H, J=6.0 Hz), 5.09 (s, 2H), 6.30 (dt, 1H, J=2.8 Hz, 8.8 Hz), 6.49 (dd, 1H, J=2.8 Hz, 11.2 Hz), 6.88 (dt, 1H, J=1.2 Hz, 8.0 Hz), 7.06 (dt, 1H, J=2.4 Hz, 8.8 Hz), 7.10 (m, 2H), 7.40 (m, 3H), 7.57 (d, 1H, J=8.0 Hz), 7.79 (d, 2H, J=8.0 Hz), 8.98 (t, 1H, J=6.0 Hz), 9.45 (s, 1H), 11.51 (s, 1H)

EXAMPLE 14

V-14 N-(4-(2-amino-5-furylphenylaminocarbonyl)phenyl)-1H-benzimidazol-2-carboxamide Following the General Method for the preparation of the final product V, a white solid of the weight 0.41 g was obtained with M-5 (0.295 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=452
1H-NMR (400 MHz, DMSO-d6) δ ppm: 4.59 (d, 2H, J=6.0 Hz), 5.09 (s, 2H), 6.30 (dt, 1H, J=2.8 Hz, 8.8 Hz), 6.49 (dd, 1H, J=2.8 Hz, 11.2 Hz), 7.06 (dt, 1H, J=2.4 Hz, 8.8 Hz), 7.10 (m, 2H), 7.40 (m, 3H), 7.73 (m, 3H), 7.57 (d, 1H, J=8.0 Hz), 7.79 (d, 2H, J=8.0 Hz), 8.98 (t, 1H, J=6.0 Hz), 9.49 (s, 1H), 11.44 (s, 1H)

EXAMPLE 15

V-15 N-(4-(2-aminophenylaminocarbonyl)phenyl)-1-naphthamide

Following the General Method for the preparation of the intermediate III, a white solid (Intermediate M-6) of the weight 2.39 g was obtained with 1-naphthoic acid (1.72 g, 10 mmol) and p-aminomethylbenzoic acid (1.51 g, 10 mmol).

Following the General Method for the preparation of the final product V, a white solid of the weight 0.291 g was obtained with M-6 (0.305 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=396

1H-NMR (400 MHz, DMSO-d6) δ ppm: 4.60 (d, 2H, J=6.0 Hz), 5.11 (s, 2H), 6.35 (dt, 1H, J=2.8 Hz, 8.4 Hz), 6.55 (dd, 1H, J=2.8 Hz, 9.6 Hz), 6.79 (m, 1H), 7.14 (t, 1H, J=6.8 Hz), 7.57 (m, 5H), 7.68 (dd, 1H, J=0.8 Hz, 7.2 Hz), 8.01 (m, 4H), 8.22 (t, 1H, J=5.6 Hz), 9.10 (s, 1H), 9.51 (s, 1H)

EXAMPLE 16

V-16 N-(4-(3-aminopyridine-4-carbamoyl)phenyl)-1-naphthamide

Following the General Method for the preparation of the final product V, a white solid of the weight 0.332 g was obtained with M-6 (0.305 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol).

MS (ESI): [M+H]+=397

1H-NMR (400 MHz, DMSO-d6) δ ppm: 4.42 (d, 2H, J=6.0 Hz), 5.11 (s, 2H), 6.35 (dt, 1H, J=2.8 Hz, 8.4 Hz), 6.50 (dd, 1H, J=2.8 Hz, 9.6 Hz), 7.14 (t, 1H, J=6.8 Hz), 7.57 (m, 5H), 7.68 (dd, 1H, J=0.8 Hz, 7.2 Hz), 8.01 (m, 4H), 8.62 (t, 1H, J=5.6 Hz), 9.10 (s, 1H), 9.58 (s, 1H)

EXAMPLE 17

V-17 N-(4-(2-amino-5-fluorophenylaminocarbonyl)phenyl)-1-naphthamide

Following the General Method for the preparation of the final product V, a white solid of the weight 0.302 g was obtained with M-6 (0.305 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=414

1H-NMR (400 MHz, DMSO-d6) δ ppm: 4.62 (d, 2H, J=6.0 Hz), 5.17 (s, 2H), 6.35 (dt, 1H, J=2.8 Hz, 8.4 Hz), 6.55 (dd, 1H, J=2.8 Hz, 11.2 Hz), 7.14 (t, 1H, J=6.8 Hz), 7.57 (m, 5H), 7.68 (dd, 1H, J=0.8 Hz, 7.2 Hz), 8.01 (m, 4H), 8.22 (t, 1H, J=5.6 Hz), 9.10 (s, 1H), 9.51 (s, 1H)

EXAMPLE 18

V-18 N-(4-(2-aminophenylaminocarbonyl)phenyl)-5-fluoro-1H-indole-2-carboxamide Following the General Method for the preparation of the intermediate III, a white solid (Intermediate M-7) of the weight 2.31 g was obtained with 5-fluoro-1H-indole-2-carboxylic acid (1.79 g, 10 mmol) and p-aminomethylbenzoic acid (1.51 g, 10 mmol).

Following the General Method for the preparation of the final product V, V-18 as a white solid of the weight 0.341 g was obtained with M-7 (0.312 g, 1 mmol), o-phenylenediamine (0.108 g, 1 mmol), HBTU (0.379 g, 1 mmol), N,N-dimethylformamide (10 ml), and triethylamine (0.202 g, 2 mmol).

V-18 of 0.21 g is dissolved in hot ethanol, followed by adding malic acid/ethanol solution dropwise and cooling to precipitate 0.16 g of the malate of V-18, compound V-18' as a white solid.

MS (ESI): [M+H]+=403

1H-NMR (400 MHz, DMSO-d6) δ ppm: 4.58 (d, 2H, J=6.0 Hz), 4.83 (s, 2H), 6.59 (dt, 1H, J=1.2 Hz, 7.6 Hz), 6.77 (dd, 1H, J=0.8 Hz, 8.0 Hz), 6.95 (dt, 1H, J=1.2 Hz, 7.6 Hz), 7.05 (dd, 1H, J=2.8 Hz, 8.4 Hz), 7.18 (m, 2H), 7.47 (m, 4H), 7.95 (d, 2H, J=8.4 Hz), 9.08 (t, 1H, J=6.0 Hz), 9.56 (s, 1H), 11.65 (s, 1H)

EXAMPLE 19

V-19 N-(4-(2-aminophenylaminocarbonyl)phenyl)-5-methyl-1H-indole-2-carboxamide Following the General Method for the preparation of the intermediate III, a white solid (Intermediate M-8) of the weight 2.77 g was obtained with 5-methyl-1H-indole-2-carboxylic acid (1.75 g, 10 mmol) and p-aminomethylbenzoic acid (1.51 g, 10 mmol).

Following the General Method for the preparation of the final product V, a white solid of the weight 0.321 g was obtained with M-8 (0.308 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=399

1H-NMR (400 MHz, DMSO-d6) δ ppm: 3.07 (s, 3H), 4.51 (d, 2H, J=6.0 Hz), 4.83 (s, 2H), 6.59 (dt, 1H, J=1.2 Hz, 7.6 Hz), 6.67 (dd, 1H, J=0.8 Hz, 8.0 Hz), 6.90 (dt, 1H, J=1.2 Hz, 7.6 Hz), 7.05 (dd, 1H, J=2.8 Hz, 8.4 Hz), 7.18 (m, 2H), 7.47 (m, 4H), 7.95 (d, 2H, J=8.4 Hz), 9.08 (t, 1H, J=6.0 Hz), 9.56 (s, 1H), 11.65 (s, 1H)

EXAMPLE 20

V-20 N-(4-(2-aminophenylaminocarbonyl)phenyl)-5-trifluoromethyl-1H-indole-2-carboxamide Following the General Method for the preparation of the intermediate III, a white solid (Intermediate M-9) of the weight 2.87 g was obtained with 5-trifluoromethyl-1H-indole-2-carboxylic acid (2.29 g, 10 mmol) and p-aminomethylbenzoic acid (1.51 g, 10 mmol).

Following the General Method for the preparation of the final product V, a white solid V-20 of the weight 0.366 g was obtained with M-9 (0.362 g, 1 mmol), o-phenylenediamine (0.108 g, 1 mmol), HBTU (0.379 g, 1 mmol), N,N-dimethylformamide (10 ml), and triethylamine (0.202 g, 2 mmol).

The above white solid V-20 of 0.26 g is dissolved in hot ethanol, followed by adding maleic acid/ethanol solution dropwise and cooling to precipitate 0.27 g of the maleate of V-20, compound V-20' as a white solid.

MS (ESI): [M+H]+=453

1H-NMR (400 MHz, DMSO-d6) δ ppm: 4.59 (d, 2H, J=6.0 Hz), 5.11 (s, 2H), 7.04 (dt, 1H, J=1.2 Hz, 9.6 Hz), 7.18 (s, 1H), 7.47 (m, 5H), 7.79 (d, 1H, J=5.2 Hz), 7.94 (d, 2H, J=8.4 Hz), 8.10 (s, 1H), 9.10 (t, 1H, J=6.0 Hz), 9.65 (s, 1H), 11.65 (s, 1H)

EXAMPLE 21

V-21 N-(4-(2-aminophenylaminocarbonyl)phenyl)-3-methoxybenzofuran-2-carboxamide

Following the General Method for the preparation of the intermediate III, a white solid (Intermediate M-10) of the weight 2.67 g was obtained with 3-methoxybenzofuran-2-carboxylic acid (1.92 g, 10 mmol) and p-aminomethylbenzoic acid (1.51 g, 10 mmol).

Following the General Method for the preparation of the final product V, a white solid of the weight 0.311 g was obtained with M-10 (0.325 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=416

H-NMR (400 MHz, DMSO-d6) δ ppm: 3.83 (s, 3H), 4.57 (d, 2H, J=5.6 Hz), 5.16 (s, 2H), 6.35 (dt, 1H, J=2.8 Hz, 8.4 Hz), 6.55 (dd, 2H, J=2.8 Hz, 10.8 Hz), 7.43 (m, 4H), 7.94 (d, 2H, J=8.0 Hz), 8.20 (s, 1H), 8.89 (t, 1H, J=5.6 Hz), 9.49 (s, 1H), 11.27 (s, 1H)

EXAMPLE 22

V-22 N-(4-(2-aminophenylaminocarbonyl)phenyl)-5-methylamino-1H-indole-2-carboxamide Following the General Method for the preparation of the intermediate III, a white solid (Intermediate M-11) of the weight 2.61 g was obtained with 5-methylamino-1H-indole-2-carboxylic acid (1.90 g, 10 mmol) and p-aminomethylbenzoic acid (1.51 g, 10 mmol).

Following the General Method for the preparation of the final product V, a white solid of the weight 0.324 g was obtained with M-11 (0.323 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=414

H-NMR (400 MHz, DMSO-d6) δ ppm: 2.83 (s, 3H), 4.58 (d, 2H, J=6.0 Hz), 4.83 (s, 2H), 6.59 (dt, 1H, J=1.2 Hz, 7.6 Hz), 6.77 (dd, 1H, J=0.8 Hz, 8.0 Hz), 6.95 (dt, 1H, J=1.2 Hz, 7.6 Hz), 7.05 (dd, 1H, J=2.8 Hz, 8.4 Hz), 7.18 (m, 2H), 7.47 (m, 5H), 7.95 (d, 2H, J=8.4 Hz), 9.08 (t, 1H, J=6.0 Hz), 9.56 (s, 1H), 11.65 (s, 1H)

EXAMPLE 23

V-23 N-(4-(2-aminophenylaminocarbonyl)phenyl)-5-amino-1H-indole-2-carboxamide

Following the General Method for the preparation of the intermediate III, a white solid (Intermediate M-12) of the weight 1.61 g was obtained with 5-amino-1H-indole-2-carboxylic acid (1.76 g, 10 mmol) and p-aminomethylbenzoic acid (1.51 g, 10 mmol).

Following the General Method for the preparation of the final product V, a white solid of the weight 0.124 g was obtained with M-12 (0.309 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=400

H-NMR (400 MHz, DMSO-d6) δ ppm: 4.58 (d, 2H, J=6.0 Hz), 4.62 (m, 2H), 4.83 (s, 2H), 6.60 (dt, 1H, J=1.2 Hz, 7.6 Hz), 6.78 (dd, 1H, J=1.2 Hz, 7.6 Hz), 6.85 (dd, 1H, J=2.4 Hz, 8.8 Hz), 6.97 (6.60 (dt, 1H, J=1.2 Hz, 7.6 Hz), 7.10 (m, 2H), 7.18 (d, 1H, J=7.6 Hz), 7.33 (d, 1H, J=8.8 Hz), 7.46 (d, 2H, J=8.0 Hz), 7.95 (d, 2H, J=8.0 Hz), 8.99 (t, 1H, J=6.0 Hz), 9.56 (s, 1H), 11.38 (s, 1H)

EXAMPLE 24

V-24 N-(4-(2-aminophenylaminocarbonyl)phenyl)benzothiophene-2-carboxamide

Following the General Method for the preparation of the intermediate III, a white solid (Intermediate M-13) of the weight 2.54 g was obtained with benzothiophene-2-carboxylic acid (1.78 g, 10 mmol) and p-aminomethylbenzoic acid (1.51 g, 10 mmol).

Following the General Method for the preparation of the final product V, a white solid of the weight 0.354 g was obtained with M-13 (0.311 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=402

H-NMR (400 MHz, DMSO-d6) δ ppm: 4.51 (d, 2H, J=6.0 Hz), 4.82 (s, 2H), 6.60 (t, 1H, J=7.2 Hz), 6.78 (d, 1H, J=7.2 Hz), 6.92 (dt, 1H, J=1.2 Hz, 8.0 Hz), 7.11 (d, 1H, J=7.2 Hz), 7.45 (m, 5H), 7.94 (m, 3H), 8.10 (s, 1H), 8.33 (t, 1H, J=6.0 Hz), 9.57 (s, 1H)

EXAMPLE 25

V-25 5-acetamido-N-(4-(2-aminophenylaminocarbonyl)phenyl)-1H-indole-2-carboxamide Following the General Method for the preparation of the intermediate III, a white solid (Intermediate M-14) of the weight 3.04 g was obtained with 5-acetamido-1H-indole-2-carboxylic acid (2.18 g, 10 mmol) and p-aminomethylbenzoic acid (1.51 g, 10 mmol).

Following the General Method for the preparation of the final product V, a white solid of the weight 0.368 g was obtained with M-14 (0.351 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=442

H-NMR (400 MHz, DMSO-d6) δ ppm: 2.10 (s, 3H), 4.59 (d, 2H, J=6.0 Hz), 5.11 (s, 2H), 5.77 (m, 1H), 7.04 (dt, 1H, J=1.2 Hz, 9.6 Hz), 7.11 (s, 1H), 7.49 (m, 5H), 7.79 (d, 1H, J=5.2 Hz), 7.94 (d, 2H, J=8.4 Hz), 8.10 (s, 1H), 9.10 (t, 1H, J=6.0 Hz), 10.01 (s, 1H), 9.65 (s, 1H), 11.65 (s, 1H)

EXAMPLE 26

V-26 5-acetyl-N-(4-(2-aminophenylaminocarbonyl)phenyl)-1H-indole-2-carboxamide

Following the General Method for the preparation of the intermediate III, a white solid (Intermediate M-15) of the weight 2.84 g was obtained with 5-acetyl-1H-indole-2-carboxylic acid (2.03 g, 10 mmol) and p-aminomethylbenzoic acid (1.51 g, 10 mmol).

Following the General Method for the preparation of the final product V, a white solid of the weight 0.311 g was obtained with M-15 (0.336 g, 1 mmol), o-phenylenediamine (0.108 g, 1 mmol), HBTU (0.379 g, 1 mmol), N,N-dimethylformamide (10 ml), and triethylamine (0.202 g, 2 mmol).

MS (ESI): [M+H]+=427

H-NMR (400 MHz, DMSO-d6) δ ppm: 2.44 (s, 3H), 4.58 (d, 2H, J=6.0 Hz), 4.83 (s, 2H), 6.59 (dt, 1H, J=1.2 Hz, 7.6

Hz), 6.77 (dd, 1H, J=0.8 Hz, 8.0 Hz), 6.95 (dt, 1H, J=1.2 Hz, 7.6 Hz), 7.05 (dd, 1H, J=2.8 Hz, 8.4 Hz), 7.18 (m, 2H), 7.47 (m, 4H), 7.95 (d, 2H, J=8.4 Hz), 9.08 (t, 1H, J=6.0 Hz), 9.56 (s, 1H), 11.65 (s, 1H)

EXAMPLE 27

V-27 N-(4-(2-amino-5-fluorophenylaminocarbonyl) phenyl)benzothiophene-2-carboxamide Following the General Method for the preparation of the final product V, a white solid of the weight 0.327 g was obtained with M-13 (0.311 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol).

MS (ESI): [M+H]+=420

H-NMR (400 MHz, DMSO-d6) δ ppm: 4.57 (d, 2H, J=6.0 Hz), 5.16 (s, 2H), 7.04 (dt, 1H, J=2.8 Hz, 8.4 Hz), 6.55 (dd, 1H, J=2.8 Hz, 11.2 Hz), 7.13 (t, 1H, J=8.4 Hz), 7.45 (m, 4H), 8.01 (m, 4H), 8.15 (s, 1H), 9.33 (t, 1H, J=5.6 Hz), 9.51 (s, 1H)

EXAMPLE 28

V-28 N-(4-(3-aminopyridine-4-carbamoyl)phenyl) benzothiophene-2-carboxamide

Following the General Method for the preparation of the final product V, a white solid of the weight 0.354 g was obtained with M-13 (0.311 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol).

MS (ESI): [M+H]+=403

H-NMR (400 MHz, DMSO-d6) δ ppm: 4.57 (d, 2H, J=6.4 Hz), 4.82 (s, 2H), 6.60 (t, 1H, J=7.2 Hz), 6.78 (d, 1H, J=7.2 Hz), 6.97 (dt, 1H, J=1.2 Hz, 8.0 Hz), 7.17 (d, 1H, J=7.2 Hz), 7.45 (m, 4H), 7.94 (m, 3H), 8.13 (s, 1H), 8.33 (t, 1H, J=6.0 Hz), 9.57 (s, 1H)

EXAMPLE 29

Test on the In Vitro Inhibitory Activities of the Compounds Towards HDACs

The test was conducted according to the instructions in the HDAC Inhibitor Drug Screening Kit (Biovision/Catalog #50051, BPS).

(1) The compounds to be tested were each individually prepared as 10 μM and 1 μM solutions and their inhibitory activities towards HDAC1 at these concentrations were tested. Results are as follows:

TABLE 2

In vitro inhibitory effects of the compounds towards HDAC1

|  | 10 μM | | 1 μM | |
| --- | --- | --- | --- | --- |
|  | % Inhibition | SD | % Inhibition | SD |
| MS-275 | 68.04 | 0.26 | 45.73 | 7.94 |
| V-1 | 15.18 | 2.82 | 4.49 | 6.71 |
| V-2 | 46.92 | 2.38 | 28.78 | 6.82 |
| V-3 | 60.02 | 4.11 | 33.28 | 5.55 |
| V-4 | 44.84 | 2.22 | 24.66 | 6.80 |
| V-5 | 81.08 | 2.26 | 59.57 | 2.45 |
| V-6 | 74.46 | 0.96 | 68.48 | 2.59 |
| V-7 | 53.28 | 1.24 | 41.39 | 2.93 |
| V-8 | 79.52 | 0.48 | 62.19 | 0.26 |
| V-9 | 69.12 | 0.23 | 37.87 | 1.88 |
| V-10 | 75.38 | 1.84 | 58.90 | 0.95 |

TABLE 2-continued

In vitro inhibitory effects of the compounds towards HDAC1

|  | 10 μM | | 1 μM | |
| --- | --- | --- | --- | --- |
|  | % Inhibition | SD | % Inhibition | SD |
| V-11 | 58.45 | 3.51 | 38.07 | 1.47 |
| V-12 | 28.41 | 3.32 | 8.70 | 3.29 |
| V-13 | 23.87 | 4.90 | 13.39 | 1.40 |
| V-14 | 87.21 | 0.27 | 74.80 | 0.91 |
| V-15 | 67.55 | 1.88 | 29.83 | 4.19 |
| V-16 | 85.06 | 0.43 | 62.51 | 4.24 |
| V-17 | 76.21 | 0.25 | 54.05 | 0.95 |
| V-18 | 49.47 | 4.66 | 22.13 | 0.03 |
| V-19 | 84.00 | 0.94 | 73.10 | 0.29 |
| V-20 | 72.24 | 2.19 | 39.40 | 1.00 |
| V-21 | 68.82 | 1.43 | 34.37 | 2.47 |
| V-22 | 59.49 | 2.65 | 36.77 | 2.50 |
| V-23 | 78.84 | 0.88 | 67.08 | 9.07 |
| V-24 | 67.38 | 0.12 | 59.13 | 1.37 |
| V-25 | 76.18 | 1.90 | 53.88 | 2.83 |
| V-26 | 70.77 | 2.60 | 59.28 | 0.90 |
| V-27 | 80.25 | 2.30 | 47.64 | 4.06 |
| V-28 | 77.38 | 3.84 | 53.53 | 4.28 |

(2) The compound to be tested was diluted using DMSO with a four times dilution method to give 10 diluted concentrations, i.e. 500 μM, 125 μM, 31.25 μM, 7.81 μM, 1.95 μM, 0.49 μM, 0.12 μM, 0.03 μM, 7.6 E-03 μM and 1.9 E-03 μM in sequence. Each dilution sample was placed in two wells and the enzyme inhibition $IC_{50}$ of the compound was tested.

TABLE 3

$IC_{50}$ of the compounds for the in vitro inhbition of HDAC

| Compound I.D | HDACs $IC_{50}$ (μM) | HDAC1 $IC_{50}$ (nM) |
| --- | --- | --- |
| MS-275 | 3.52 | 668 |
| V-5 | 3.29 | 212 |
| V-6 | 7.79 | 344 |
| V-8 | 1.83 | 732 |
| V-9 | 3.99 | 178 |
| V-10 | 7.76 | 1612 |
| V-14 | 4.91 | 330 |
| V-15 | 1.04 | 517 |
| V-16 | 3.11 | 276 |
| V-17 | 0.92 | 735 |
| V-19 | 1.14 | 414 |
| V-20 | 3.77 | 1007 |
| V-21 | 9.40 | 758 |
| V-23 | 6.89 | 998 |
| V-24 | 1.72 | 1579 |
| V-25 | 1.02 | 301 |
| V-26 | 1.37 | 509 |
| V-27 | 1.22 | 276 |
| V-28 | 1.31 | 731 |

EXAMPLE 30

Test on the In Vitro Inhibitory Activities of the Compounds Towards Tumor Cells

The inhibitory activities of the compounds towards Hut78 T lymphocytic leukemia cells, Jurkat E6-1 human T-cell lymphoma, A549 human lung cancer cells, K562 human chronic myelogenous leukemia cells, Hep3B2.1-7 human liver cancer cells, MDA-MB-435s human breast cancer cells, Colo320 human rectal cancer cell line, and PC-3 human prostate cancer were determined. The inhibition percentages as represented by $IC_{50}$ values were obtained through CCK-8 method. Detailed results are as follows:

TABLE 4

Determination of the IC$_{50}$ values for in vitro anti-proliferative effects of the compounds on tumor cell strains

| Compound | PC-3 | MDA-MB-435S | A549 | Colo320 | Hep3B | Hut78 | K562 | Jurkat E6-1 |
|---|---|---|---|---|---|---|---|---|
| MS-275 | 0.5020 | 2.707 | 2.278 | 0.5222 | 6.816 | 0.5281 | 4.663 | 0.5614 |
| V-5 | 0.242 | | 2.636 | 2.450 | 3.461 | 0.0194 | 1.312 | 0.179 |
| V-6 | 0.370 | | 1.248 | 3.133 | 3.068 | 0.0088 | 2.092 | 0.128 |
| V-9 | 2.236 | 14.76 | 21.23 | | 15.89 | 3.462 | 17.11 | 2.132 |
| V-14 | | | 3.136 | | 1.523 | 0.3557 | 0.4369 | 0.4578 |
| V-15 | 2.630 | | | 0.5344 | 2.760 | 2.778 | 2.884 | 1.369 |
| V-16 | | | | 86.03 | 3.363 | 1.789 | 6.080 | |
| V-19 | 0.1914 | | | | 10.22 | 1.188 | 1.908 | |
| V-25 | 0.069 | | 0.2953 | | | 0.877 | | |
| V-26 | 12.17 | | 29.92 | 88.405 | 52.172 | 0.2311 | 19.851 | 12.353 |
| V-27 | 3.568 | | 5.089 | 26.997 | 15.997 | 0.0558 | 2.811 | 1.392 |

EXAMPLE 31

Test of Maximum Tolerance Dose as a Measure of the Compounds' Toxicity Through Intragastrical Administration Forty ICR mice, half female and half male, weighing 18-20 g were divided into four groups, 10 mice in each group. After the mice were fasted for 6 h, the compound to be tested was administrated intragastrically to each group at a volume of 0.3 ml/10 g by using a sterile plastic syringe. General physical signs and the deaths of the animals were recorded at 1, 2 and 4 h after the administration. The animals were then observed continuously for 14 days and their weights, physical signs and deaths were observed and recorded every day. Dead animals were dissected to see if there was any visible pathological change in the animal's viscera and pathological examination was performed on suspicious tissues and organs. A part of the experimental results is as follows.

The maximum tolerance doses of Compounds V-5, V-6, V-9, V-14, V-16, V-19, V-25, V-26 and V-27 are all above 2000 mg/kg.

EXAMPLE 32

Effects of the Compounds on hERG Potassium Channel

TABLE 5

Experimental results about the effects of the compounds on hERG potassium channel

| Compound | Half inhibition concentration for the effect on hERG potassium current IC$_{50}$ (μM) | Maximum inhibition percentage at 10 μM (%) |
|---|---|---|
| V-5 | >10 | 11.5 ± 0.8 |
| V-9 | >10 | 19.9 ± 6.7 |

EXAMPLE 33

Preliminary Pharmacokinetic Experiment for the Compounds

TABLE 6

Preliminary pharmacokinetic results of the compounds

| Compound | Intravenous half-life in hours (rat, 2 mg/kg, i.v.) | Oral half-life in hours | Oral bioavailability % |
|---|---|---|---|
| V-5 | 1.27 | 3.70 | 7.84 |
| V-9 | 0.95 | 6.37 | 28.8 |

EXAMPLE 34

| Tablet: | |
|---|---|
| The compound of any one of Examples 1-48 | 10 mg |
| Sucrose | 150 mg |
| Corn starch | 38 mg |
| Calcium stearate | 2 mg |

Preparation method: The active ingredient, sucrose and corn starch can be mixed, wetted by adding water and stirred thoroughly to obtain a homogenous mixture which can be dried, grounded and sieved. Then calcium stearate can be added and mixed homogenously before pressing to form a tablet. Each tablet weighs 200 mg, containing 10 mg active ingredient.

EXAMPLE 35

| Injection: | |
|---|---|
| The compound of any one of Examples 1-48 | 20 mg |
| Water for injection | 80 mg |

Preparation method: The active ingredient can be dissolved in water for injection, mixed homogenously and filtered. The resultant solution can be dispensed into ampoules under aseptic conditions, 10 mg in each ampoule with 2 mg active ingredient therein.

The invention claimed is:
1. A compound selected from the group consisting of:
V-1 N-(4-(2-aminophenylaminocarbonyl)phenyl)-2-naphthamide,
V-2 N-(4-(2-amino-5-fluorophenylaminocarbonyl)phenyl)-2-naphthamide,
V-2' N-(4-(2-amino-5-fluorophenylaminocarbonyl)phenyl)-2-naphthamide hydrochloride,
V-3 N-(4-(2-aminophenylaminocarbonyl)phenyl)-6-methoxy-2-naphthamide,
V-4 N-(4-(2-amino-5-fluorophenylaminocarbonyl)phenyl)-6-methoxy-2-naphthamide,
V-5 N-(4-(2-aminophenylaminocarbonyl)phenyl)-1H-indole-2-carboxamide,
V-5' N-(4-(2-aminophenylaminocarbonyl)phenyl)-1H-indole-2-carboxamide hydrobromide,
V-6 N-(4-(3-aminopyridine-4-carbamoyl)phenyl)-1H-indole-2-carboxamide,
V-6' N-(4-(3-aminopyridine-4-carbamoyl)phenyl)-1H-indole-2-carboxamide sulfate,
V-7 N-(4-(2-amino-5-fluorophenylaminocarbonyl)phenyl)-1H-indole-2-carboxamide,
V-8 N-(4-(2-aminophenylaminocarbonyl)phenyl)benzofuran-2-carboxamide,
V-8' N-(4-(2-aminophenylaminocarbonyl)phenyl)benzofuran-2-carboxamide mesylate,
V-9 N-(4-(2-amino-5-fluorophenylaminocarbonyl)phenyl)benzofuran-2-carboxamide,
V-10 N-(4-(2-amino-5-thienylphenylaminocarbonyl)phenyl)benzofuran-2-carboxamide,
V-11 N-(4-(2-amino-5-phenylphenylaminocarbonyl)phenyl)benzofuran-2-carboxamide,
V-12 N-(4-(2-aminophenylaminocarbonyl)phenyl)-1H-benzimidazol-2-carboxamide,
V-13 N-(4-(2-amino-5-fluorophenylaminocarbonyl)phenyl)-1H-benzimidazol-2-carboxamide,
V-13' N-(4-(2-amino-5-fluorophenylaminocarbonyl)phenyl)-1H-benzimidazol-2-carboxamide trifluoroacetate,
V-14 N-(4-(2-amino-5-furylphenylaminocarbonyl)phenyl)-1H-benzimidazol-2-carboxamide,
V-15 N-(4-(2-aminophenylaminocarbonyl)phenyl)-1-naphthamide,
V-16 N-(4-(3-aminopyridine-4-carbamoyl)phenyl)-1-naphthamide,
V-17 N-(4-(2-amino-5-fluorophenylaminocarbonyl)phenyl)-1-naphthamide,
V-18 N-(4-(2-aminophenylaminocarbonyl)phenyl)-5-fluoro-1H-indole-2-carboxamide,
V-18' N-(4-(2-aminophenylaminocarbonyl)phenyl)-5-fluoro-1H-indole-2-carboxamide malate,
V-19 N-(4-(2-aminophenylaminocarbonyl)phenyl)-5-methyl-1H-indole-2-carboxamide,
V-20 N-(4-(2-aminophenylaminocarbonyl)phenyl)-5-trifluoromethyl-1H-indole-2-carboxamide,
V-20' N-(4-(2-aminophenylaminocarbonyl)phenyl)-5-trifluoromethyl-1H-indole-2-carboxamide maleate,
V-21 N-(4-(2-aminophenylaminocarbonyl)phenyl)-3-methoxybenzofuran-2-carboxamide,
V-22 N-(4-(2-aminophenylaminocarbonyl)phenyl)-5-methylamino-1H-indole-2-carboxamide,
V-23 N-(4-(2-aminophenylaminocarbonyl)phenyl)-5-amino-1H-indole-2-carboxamide,
V-24 N-(4-(2-aminophenylaminocarbonyl)phenyl)benzothiophene-2-carboxamide,
V-25 5-acetamido-N-(4-(2-aminophenylaminocarbonyl)phenyl)-1H-indole-2-carboxamide,
V-26 5-acetyl-N-(4-(2-aminophenylaminocarbonyl)phenyl)-1H-indole-2-carboxamide,
V-27 N-(4-(2-amino-5-fluorophenylaminocarbonyl)phenyl)benzothiophene-2-carboxamide, and
V-28 N-(4-(3-aminopyridine-4-carbamoyl)phenyl)benzothiophene-2-carboxamide; and salts thereof.

2. A pharmaceutical composition comprising a therapeutically effective amount of the compound or a salt thereof according to claim 1, and a pharmaceutically acceptable carrier.

3. A method for treating a tumor, comprising administering a therapeutically effective amount of the compound or a salt thereof according to claim 1 to a patient in need thereof.

* * * * *